US00PP31257P2

(12) United States Plant Patent
Wheeler et al.

(10) Patent No.: US PP31,257 P2
(45) Date of Patent: Dec. 24, 2019

(54) BLUEBERRY PLANT NAMED 'BB06-426MI-84'

(50) Latin Name: *Vaccinium corymbosum*
Varietal Denomination: BB06-426MI-84

(71) Applicant: Berry Blue, LLC, Grand Junction, MI (US)

(72) Inventors: Edmund J. Wheeler, Holland, MI (US); James F. Hancock, Scarborough, ME (US)

(73) Assignee: Berry Blue, LLC, Grand Junction, MI (US)

( * ) Notice: Subject to any disclaimer, the term of this patent is extended or adjusted under 35 U.S.C. 154(b) by 0 days.

(21) Appl. No.: 16/350,520

(22) Filed: Nov. 27, 2018

(51) Int. Cl.
*A01H 5/08* (2018.01)
*A01H 6/36* (2018.01)

(52) U.S. Cl.
USPC ..... Plt./157
CPC ..... *A01H 6/36* (2018.05)

(58) Field of Classification Search
USPC ..... Plt./157
See application file for complete search history.

*Primary Examiner* — Anne Marie Grunberg
(74) *Attorney, Agent, or Firm* — King IP Law; Joshua King

(57) ABSTRACT

'BB06-426MI-84' is a new and distinct variety of high chill tetraploid Northern highbush blueberry (*Vaccinium*) plant. 'BB06-426MI-84' is characterized as having large fruit, medium blue in color, that is firm with a very small and dry picking scar. The fruit is well exposed on a vigorously growing medium upright bush. Along with a small sized crown, a loose fruit cluster, concentrated ripening, and firm fruit that is easily detachable, 'BB06-426MI-84' displays characteristics suitable for mechanical harvest. The fruit shape of 'BB06-426MI-84' is oblate with a medium amount of waxy bloom that is moderately persistent following handling. The fruit has very good flavor, a balance of sweetness and acidity and is very juicy with a medium crunchy texture.

6 Drawing Sheets

Latin name: *Vaccinium corymbosum.*
Common name: Blueberry.
Cultivar name: 'BB06-426MI-84'.

BACKGROUND AND SUMMARY

Blueberries are a well-known fruit enjoyed by many throughout the world. One example of an existing commercial blueberry variety is 'Duke', unpatented. Another example of an existing, patented blueberry variety is 'Draper', U.S. Plant Pat. No. 15,103.

Comparing 'BB06-426MI-84' to 'Duke', the bush habit of 'BB06-426MI-84' is more upright, the fruit of 'BB06-426MI-84' is slightly darker in color, the maturity of 'BB06-426MI-84' is 5 days later than Duke and the mature leaves of 'BB06-426MI-84' are much darker in color.

Comparing 'BB06-426MI-84' to 'Draper', the bush habit of 'BB06-426MI-84' is more upright, the berry size and weight of 'BB06-426MI-84' are slightly less and the time of maturity of 'BB06-426MI-84' is 10 days earlier.

The present cultivar, 'BB06-426MI-84', provides one or more advantages compared to these and/or other blueberry varieties.

BRIEF DESCRIPTION OF THE PHOTOGRAPHS

DETAILED DESCRIPTION

Figure 1:
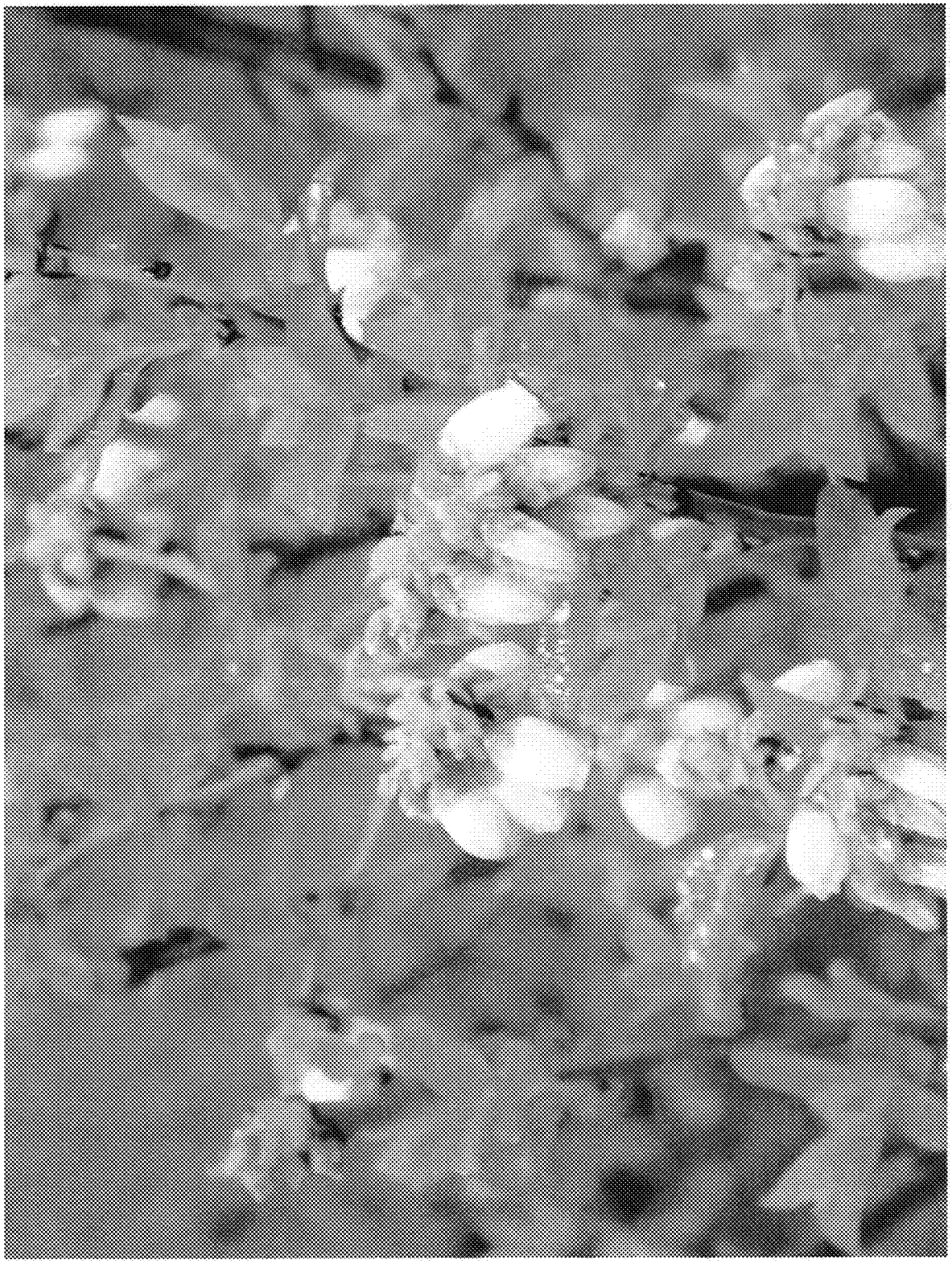
FIG. 1 is a close-up photograph of 'BB06-426MI-84' taken mid-May, 2018, Grand Junction, Mich., and showing opened and unopened flowers, their shape, color, the color of the peduncles and pedicels, shape and color of newly emerged leaves.
Figure 2:
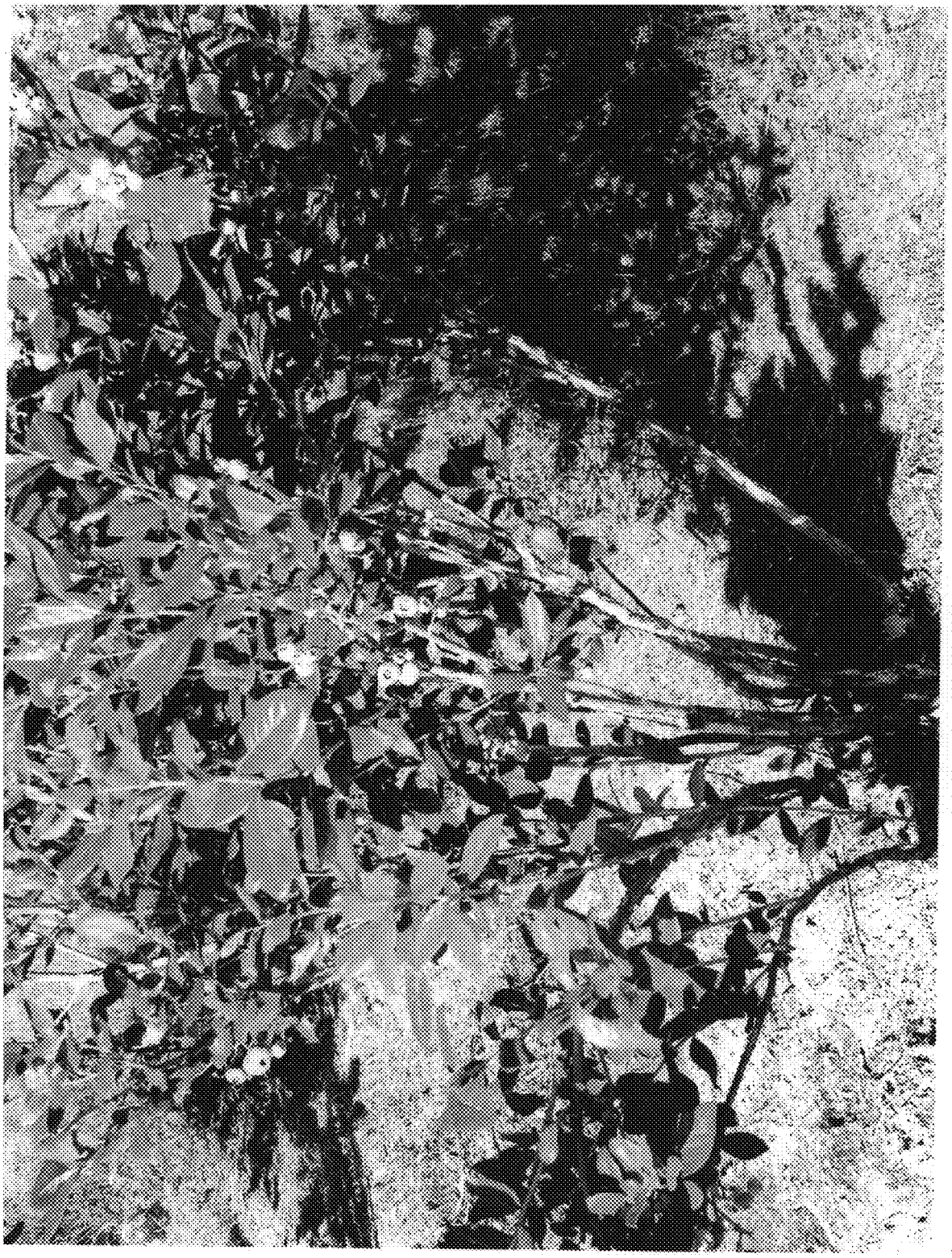
FIG. 2 is a photograph of a 5-year-old bush of 'BB06-426MI-84' taken early July, 2018, Grand Junction, Mich., and showing the bush shape, crown size, mature cane number and structure, abundance of leaves and fruit load.
Figure 3:
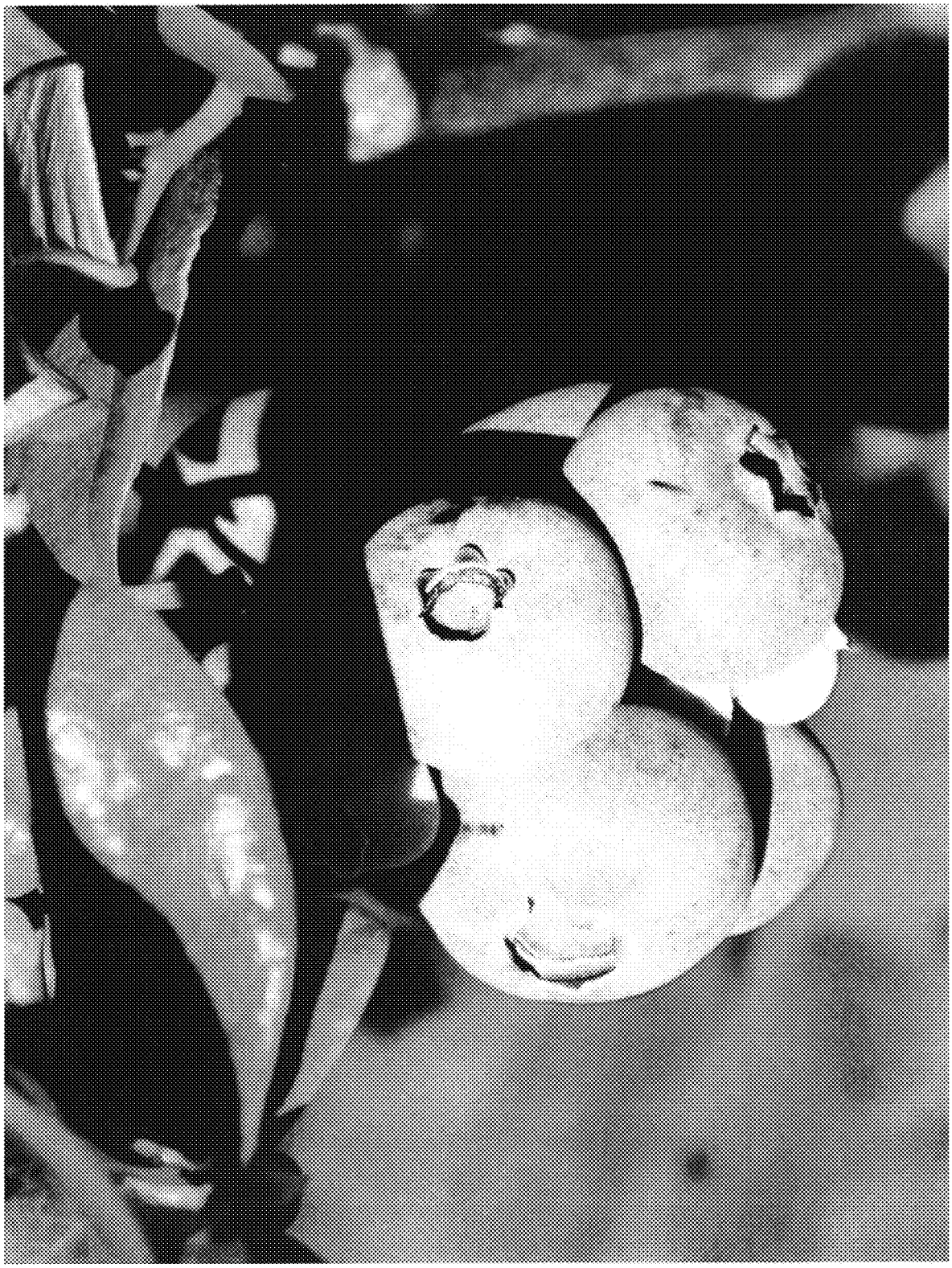
FIG. 3 is a close-up photograph of 'BB06-426MI-84', taken early July, 2018, Grand Junction, Mich., and showing ripe fruit, the shape and relative size and their color and shape, and also showing the size of the calyx.
Figure 4:
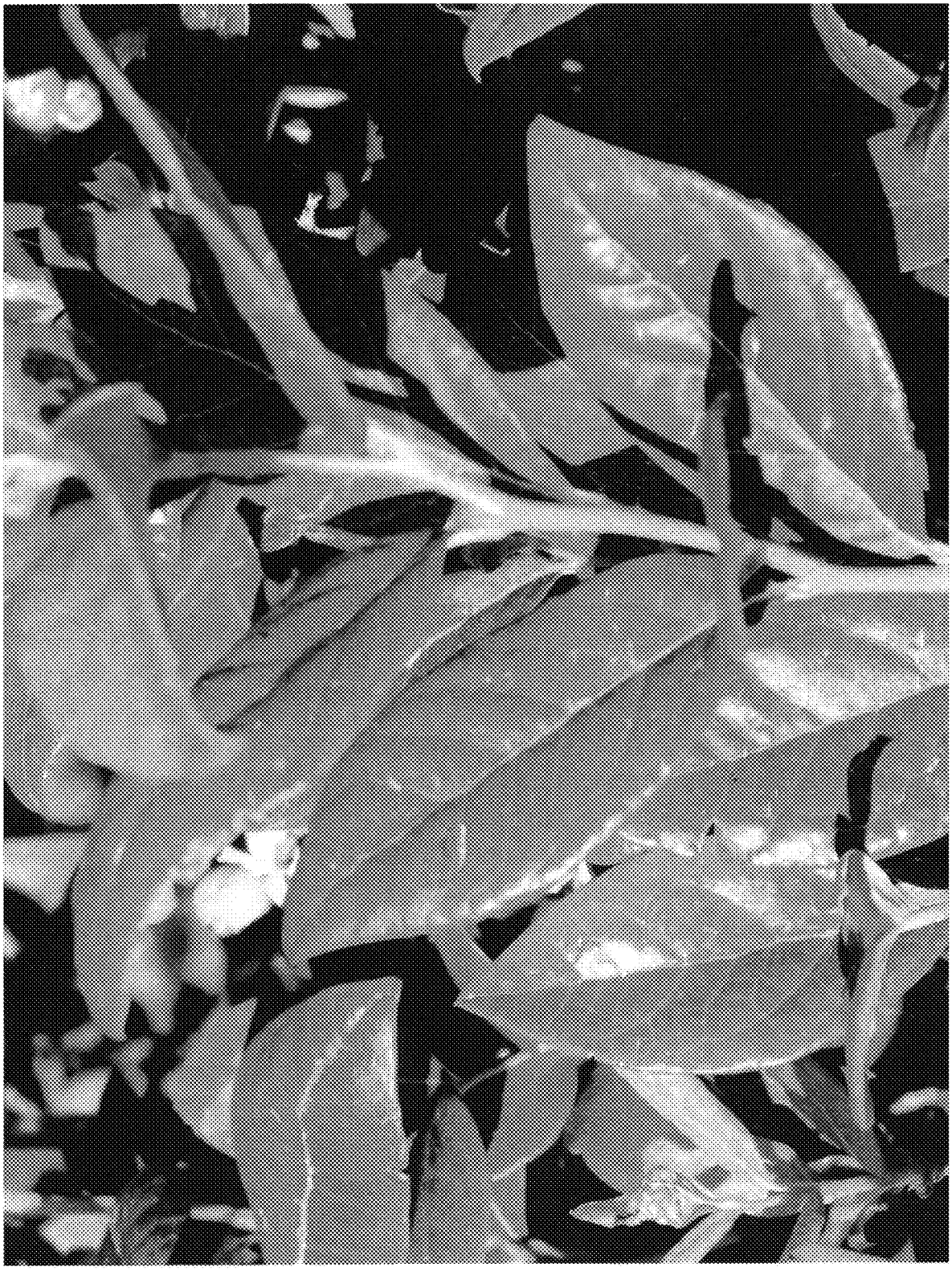
FIG. 4 is a close-up photograph of 'BB06-426MI-84', taken early July, 2018, Grand Junction, Mich., and showing the shape, size and color of mature leaves and also their venation and arrangement.
Figure 5:
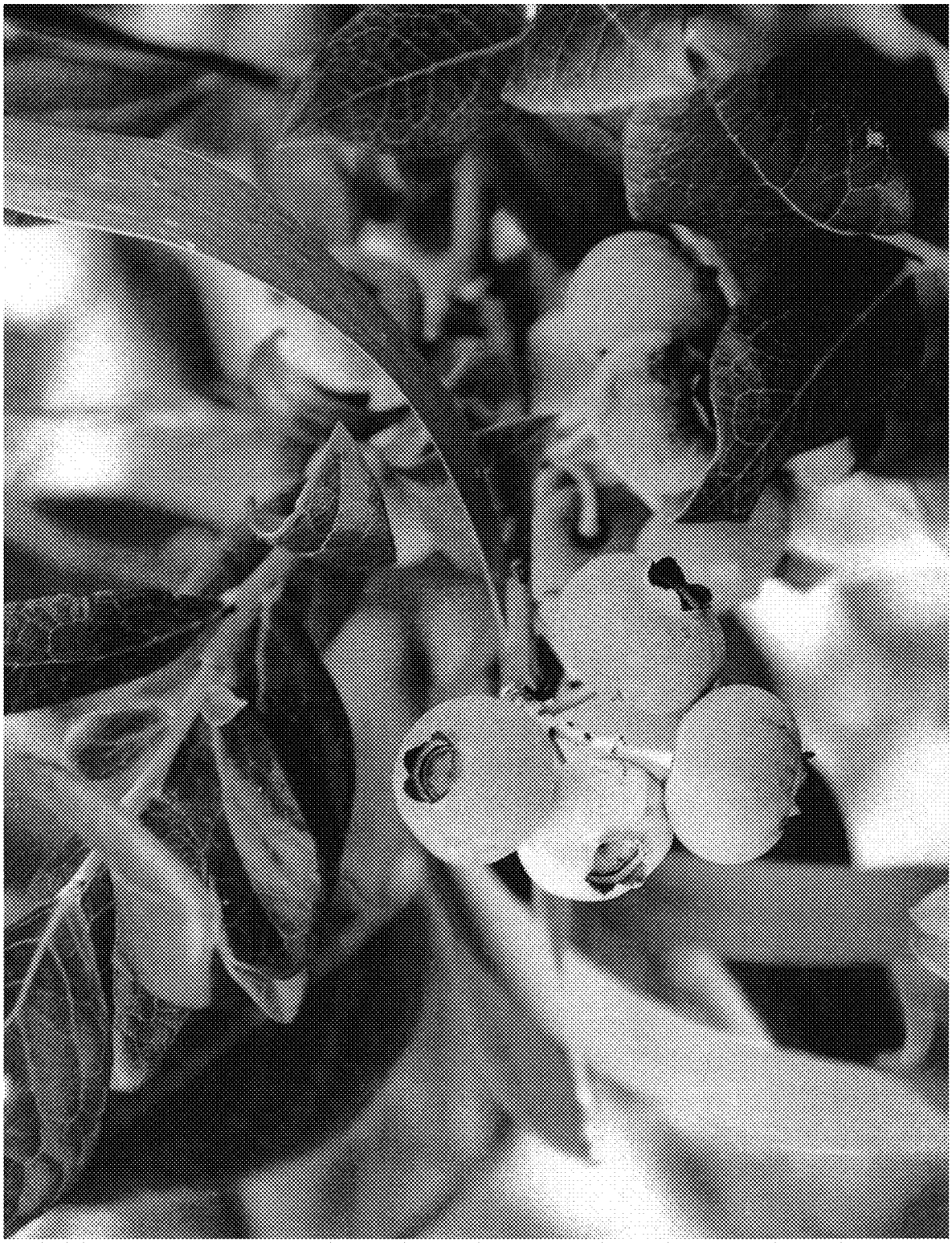
FIG. 5 is a close-up photograph of 'BB06-426MI-84', taken early July, 2018, Grand Junction, Mich., and showing the shape, size and color of ripe and unripe fruit, the sizes and colors of the peduncle and pedicels, and the color and shape of mature leaves including their venation.
Figure 6:
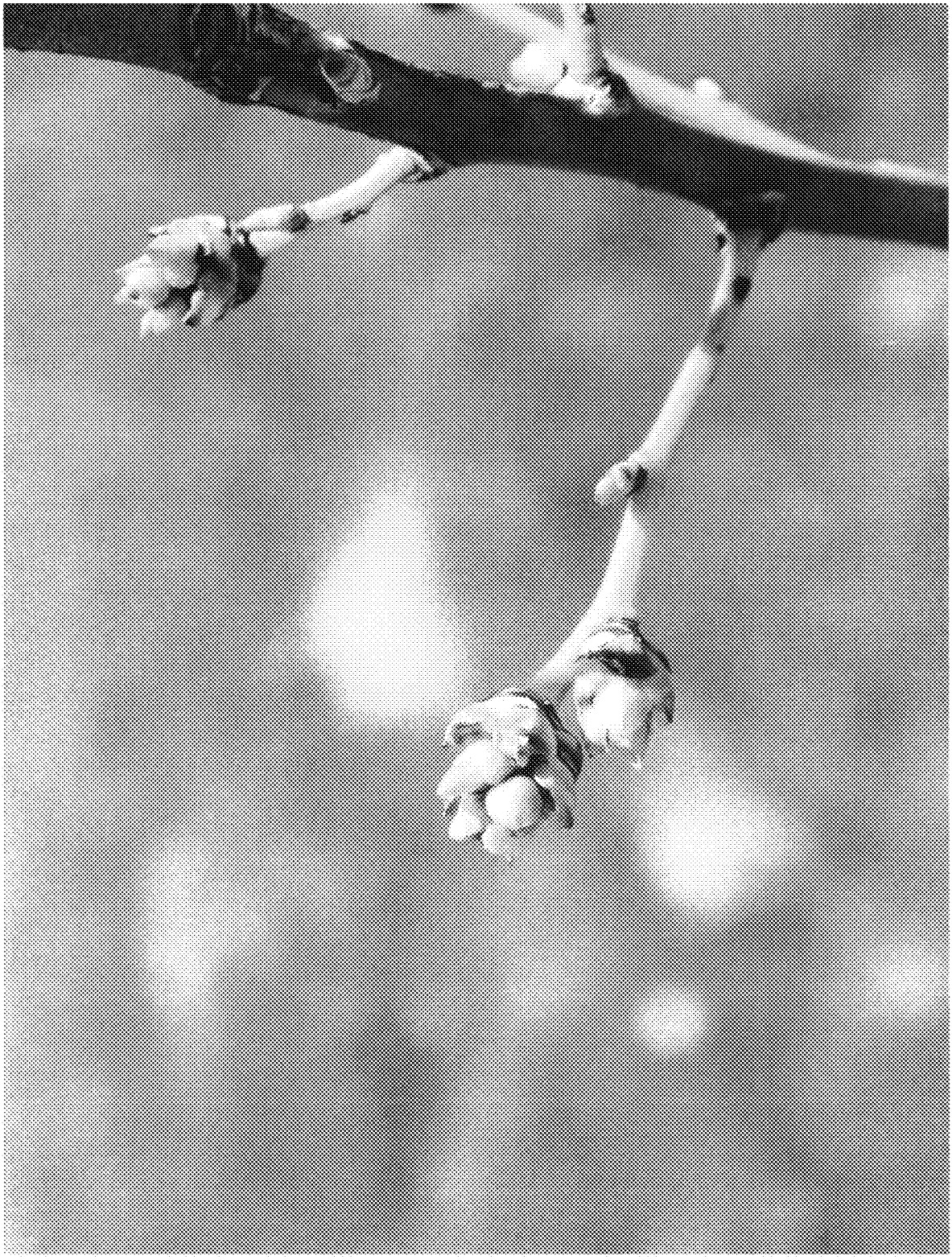
FIG. 6 is a close up photograph of 'BB06-426MI-84', taken early April, 2018, Grand Junction, Mich., and showing emerging buds in early spring including their size, shape and number, and also showing the early spring color of fruiting wood and the color and texture of 1-year old wood.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are largely based on field observations made in 2018 in advanced trial plantings on mature 6-year old bushes in Grand Junction, Mich. and 4-year old bushes in Hammonton, N.J. Laboratory analysis of fruit characteristics were done in Grand Junction, Mich. The bushes in the advanced trials were propagated from the original mother bush selected near Grand Junction, Mich., and all progeny have retained the characteristics of the original selection.

Cultivar name: 'BB06-426MI-84'.

Classification:

Family: Ericaceae.

Botanical name: *Vaccinium corymbosum.*

Common name: Blueberry.

Parentage:

Female Parent

Name 'Draper' (child of 'Duke' (unpatented) x 'G 751' (unpatented)).

U.S. Plant Pat. No. 15,103.

Compared to 'Draper', the bush habit of 'BB06-426MI-84' is more upright, the berry size and weight are slightly less than 'Draper', the time of maturity of 'BB06-426MI-84' is 10 days earlier and the time of flowering of 'BB06-426MI-84' is 10 days earlier.

Male Parent

Name: 'Bluecrop' (unpatented) (child of 'GM-37' x 'CU7', both unpatented).

United States Plant Patent: none.

Compared to 'Bluecrop', 'BB06-426MI-84' has a much more upright bush shape than 'Bluecrop'. The berries of 'BB06-426MI-84' are rounder, larger, much firmer and much less acidic than the berries of 'Bluecrop'. "The 50% ripening date is 5 days earlier and its mature leaves are much darker in color than those of 'Bluecrop'.

The cross between 'Draper' and 'Bluecrop' was made in a greenhouse in Holland, Mich. in 2006. Emasculated flowers of 'Draper' were hand pollinated with pollen from 'Bluecrop'. Seed was sown, germinated, and the plants were grown for 18 months in Grand Junction, Mich. and then planted in a seedling evaluation plot near Grand Junction, Mich. in 2008. The plant was evaluated for 4 years and first selected in 2012, based on its excellent fruit and morphological characteristics including maturity date, bush habit, berry quality, flavor, and storage ability. The bush was given the name 'BB06-426MI-84'. The bush was dug from the trial field in October 2012 and transplanted into a pot and placed in a virus-free screened greenhouse. Additional plants have been propagated by softwood cuttings and tissue culture. Five and ten bush advanced trials were planted in Grand Junction, Muskegon, Mich. and Hammonton, N.J. All of the plants propagated have retained the original characteristics.

Plants from vegetative softwood cuttings of 'BB06-426MI-84' were first propagated in 2011 in Grand Junction, Mich., and several times since as needed. Micropropagation by tissue culture was first initiated in 2013. In all cases, the propagated plants from softwood cuttings and tissue culture have retained the original characteristics. 'BB06-426MI-84' roots readily from softwood cuttings and tissue culture microshoots.

General description: 'BB06-426MI-84' is a new and distinct high chill tetraploid Northern highbush blueberry (*Vaccinium*) variety consisting of primarily *V. corymbosum*, with a limited contribution of genes from *V. angustifolium* and *V. darrowii*. It is a productive early-midseason maturing variety". 'BB06-426MI-84' is characterized as having large fruit, medium blue in color, firm with a very small and dry pedicel scar. The fruit is well exposed on a vigorously growing medium upright bush. Along with a small sized crown, a loose fruit cluster, concentrated ripening, and firm fruit that is easily detachable, 'BB06-426MI-84' displays characteristics suitable for mechanical harvest. 'BB06-426MI-84' is intended for areas that successfully grow high chill Northern highbush varieties. Ripe fruit are large, nearly 2.5 grams/berry. The mean start date of flowering for 'BB06-426MI-84' in southern Michigan is April 28. Frost protection may be needed for successful pollination and fruit set. Winter chill requirement for successful flowering and leafing is at least 1000 hours below 7° C. Leaves emerge a few days before flowering commences. The mean ripening date for 'BB06-426MI-84' is about July 10 in Grand Junction, Mich. The fruit shape of 'BB06-426MI-84' is oblate with a medium amount of waxy bloom that is moderately persistent following handling. Such fruit has very good flavor with a balance of sweetness and acidity and is very juicy with a medium crunchy texture. The fruit of 'BB06-426MI-84' has a medium storage capability of 3 weeks in refrigeration with little decay.

References to color refer to The Pantone Book of Color, Eisemann and Herbert, Harry N. Abrams, Inc. Publishers, New York, ISBN 0-8109-3711-5, 1990.

Morphological characteristics reference: Plant Systematics, Jones and Luchsinger, 2 Ed., McGraw Hill, New York, ISBN 0-07-032796-3, 1986.

Device used to measure Soluble Solids (SS-Brix°, Titratable acidity (TA), pH: PAL-BX/Acid 7, Atago USA, Inc., Bellevue, Wash.

Firmness readings—BioWorks FirmTec2, Wamena, Kans.

Average size information:

*General description.*—Medium large bush, medium upright bush shape, 6-year old bush averages 115 cm tall, 85 cm wide, height/width ratio — 1.35.

*Growth.*—Very good growth and vigor, leafing is normal and abundant.

*Productivity.*—Very good.

*Cold hardiness.*—Vegetative and flower buds −26° C., open flowers and fruit: −2° C.

Specific features of the variety:

Plant:

*Growth habit.*—Medium upright.

*Plant width.*—85 cm at mid-bush.

*Plant height.*—115 cm.

*Productivity.*—6-7 pounds per bush at maturity.

*Cold hardiness/tolerance.*—Vegetative and flower buds −26° C., open flowers and fruit: −2° C.

*Chilling requirement.*—1000 hours below 7° C.

*Canes.*—Moderately branched, 7 to 8 canes per bush, average length of 38 cm, range 35-43 cm in length, medium number of lateral branches, circular in shape, mature width 14 mm.

*Mature cane color.*—Pantone Maple Sugar 15-1316.

*Mature cane texture.*—Rough.

*Fruiting wood.*—Smooth texture; Immature winter color: Pantone Golden Cream 13-0939.

*Immature summer color.*—Pantone Parrot Green 15-0341.

*Internode length range.*—20-23 mm.

*Surface texture of new wood.*—Smooth.

*Time of beginning of leaf bud burst.*—April 19, Grand Junction, Mich.

*Time of beginning of flowering*.—April 28, Grand Junction, Mich.
*Date of* 50% *open flowers*.—May 14, Grand Junction, Mich.
*Time of beginning of fruit ripening*.—July 1, Grand Junction, Mich.
*Disease resistance/susceptibility*.—None claimed.

Foliage:
*Leaf color*.—Upper surface: Pantone Chive 19-0323; Lower surface: Pantone Peridot 17-033.
*Leaf arrangement*.—Simple alternate.
*Leaf margins*.—Entire.
*Leaf venation*.—Pinnate.
*Leaf shape*.—Elliptic.
*Leaf apices*.—Acute.
*Leaf bases*.—Acute.
*Vein and petiole coloration*.—Pantone Herbal Garden 15-0336.
*Petiole length*.—5 mm.
*Petiole diameter*.—1 mm.
*Evergreen*.—No.

Leaf dimensions:
*Overall shape*.—Elliptic.
*Length*.—Range 76-82 mm, average 80 mm.
*Width*.—Range 38-43 mm, average 40 mm.
*Leaf margins*.—Entire, no visible nectaries.
*Leaf surface*.—No visible pubescence.

Flower buds:
*Shape*.—Elliptic.
*Length*.—7 mm.
*Width*.—2 mm.
*Color*.—Pantone Raw Sienna 17-1436.

Flower:
*Flower shape*.—Urceolate.
*Flower bud number*.—Medium high.
*Flowers per cluster*.—Average 7 per cluster.
*Flower fragrance*.—Light floral.
*Corolla color*.—Pantone Silver Peony 12-1206.
*Corolla length*.—9 mm.
*Corolla width*.—6 mm.
*Corolla aperture width*.—4 mm.
*Corolla texture*.—Smooth.
*Flower peduncle length*.—8 mm.
*Peduncle diameter*.—1 mm.
*Peduncle texture*.—Smooth.
*Peduncle color*.—Pantone Pale Blush 14-1312.
*Flower pedicel length*.—4 mm.
*Pedicel diameter*.—1.5 mm.
*Pedicel texture*.—Smooth.
*Pedicel color*.—Pantone Willow Green 15-0525.
*Calyx* (*with sepals*).—2.5 mm.
*Calyx color*.—Pantone Willow Green 15-0525.
*Stamen length*.—7 mm.
*Number per flower*.—10.
*Filament color*.—Pantone Golden Glow 15-1050.
*Style*.—5 mm in length.
*Style color*.—Pantone Willow Green 15-0525.
*Pistil*.—7 mm top of ovary to stigma tip, even with top of corolla.
*Ovary color*.—Pantone Willow Green 15-0525.
*Anther length*.—4 mm.
*Number*.—10.
*Color*.—Pantone Golden Glow 15-1050.

Pollen:
*Abundance*.—Moderately abundant.
*Color*.—Pantone Cream 12-0817.

Fruit:
*Date of* 50% *maturity*.—July 10, Grand Junction, Mich.
*Duration of ripening*.—15 days.
*Yield*.—6-7 pounds per bush at maturity.
*Cluster density*.—Loose.
*Immature fruit color*.—Pantone Leaf Green 15-0332.
*Berry color with wax*.—Pantone Velvet Morning 18-3927.
*Berry color with wax removed*.—Pantone Deep Cobalt 19-3925.
*Berry flesh color*.—Pantone Frozen Dew 13-0513.
*Berry surface wax abundance*.—Medium, medium persistent.
*Berry weight*.—Average 2.5 grams/berry.
*Berry size diameter*.—Average 18 mm.
*Berry height*.—Average 13 mm.
*Berry shape*.—Oblate.
*Average number of fruit per cluster*.—6-7.
*Average weight of fruit per cluster*.—Average 17 grams.
*Detachment force*.—Easy.
*Self-fruitfulness*.—Very good.
*Fruit stem scar*.—Small, dry, 2 mm diameter.
*Calyx shape*.—5 point.
*Calyx diameter*.—4 mm.
*Calyx depth*.—2 mm.
*Berry firmness*.—Very firm, FirmTec: 214 g/mm$^2$.
*Berry sweetness*.—Medium high, Brix°=13.5.
*Berry acidity*.—Medium, titratable acidity =0.35.
*Berry flavor and texture*.—Balanced flavor of sweetness and acidity, juicy and crunchy texture.
*Storage ability*.—Excellent, storage of 3 weeks with little decay or loss of quality.
*Suitability for mechanical harvesting*.—A small bush crown, a medium upright bush shape, very firm fruit and easy detachment are desirable for mechanical harvest.

Seed:
*Seed abundance in fruit*.—Medium abundant.
*Seed color*.—Pantone Baked Clay 18-1441.
*Seed dry weight*.—NA.
*Seed size*.—0.75 mm length, 0.5 mm width.

Possible typical market uses: Fresh market, processing into jams, purees, and yogurt.

What is claimed is:

1. A new and distinct cultivar of Blueberry plant named 'BB06-426MI-84' as described and shown herein.

* * * * *